United States Patent
Gross et al.

(10) Patent No.: US 6,939,471 B2
(45) Date of Patent: Sep. 6, 2005

(54) METHOD FOR DETERMINING A TREATMENT PARAMETER ON A HAEMOFILTRATION DEVICE, AND HAEMOFILTRATION DEVICE FOR APPLYING THE METHOD

(75) Inventors: Malte Gross, Schweinfurt (DE); Andreas Maierhofer, Schweinfurt (DE)

(73) Assignee: Fresenius Medical Care Deutschland GmbH, Bad Homberg (DE)

(*) Notice: Subject to any disclaimer, the term of this patent is extended or adjusted under 35 U.S.C. 154(b) by 198 days.

(21) Appl. No.: 10/393,361

(22) Filed: Mar. 21, 2003

(65) Prior Publication Data

US 2003/0230533 A1 Dec. 18, 2003

(51) Int. Cl.$^7$ .................... B01D 61/32; B01D 61/24; B01D 61/28; A61M 1/14
(52) U.S. Cl. .................... 210/746; 210/85; 210/103; 210/134; 210/141; 210/143; 210/252; 210/258; 210/321.6; 210/321.71; 210/646; 210/647; 210/650; 210/739; 604/4.01; 604/5.01; 604/6.11
(58) Field of Search ................ 210/85, 87, 97, 210/103, 109, 134, 141, 143, 252, 258, 321.6, 321.71, 645, 646, 647, 649, 650, 651, 739, 746; 604/4.01, 5.01, 6.11

(56) References Cited

U.S. PATENT DOCUMENTS 5,744,031 A * 4/1998 Bene ............... 210/321.71

FOREIGN PATENT DOCUMENTS

| DE | 3938662 | 7/1991 |
|---|---|---|
| DE | 19747360 | 4/1999 |
| DE | 198 31 385 | 1/2000 |
| EP | 0658352 | 6/1995 |
| EP | 0930080 | 7/1999 |
| EP | 1062960 | 12/2000 |
| WO | 9832476 | 7/1998 |
| WO | 0002604 | 1/2000 |

OTHER PUBLICATIONS

Jacobs, Claude (ed.) "Operational Characteristics of the Dialyzer," *Replacement of renal function by dialysis*, pp. 38–41 (1996).

Polaschegg, H.D., "Automatic, noninvasive intradialytic clearance measurement," *International Journal of Artificial Organs*, 16(4): 185–191 (1993).

* cited by examiner

*Primary Examiner*—John Kim
(74) *Attorney, Agent, or Firm*—Jacobson Holman PLLC

(57) ABSTRACT

A method for determining a treatment parameter on a haemofiltration device, as well as a haemofiltration device for applying the method, based on the recognition that a determination method known from haemodialysis can, with little modification, be transferred to haemofiltration. To this effect a physical-chemical characteristic of the substitution fluid and of the fluid which is removed from the haemofilter by way of an ultrafiltrate outlet pipe, is determined. Furthermore, this characteristic is acquired before, after or during a change of this characteristic in the substitution fluid, and is evaluated. As a result, the ion dialysance and thus the urea clearance of a haemofiltration device, which can also be operated as a haemodiafiltration device, can be determined.

30 Claims, 3 Drawing Sheets

METHOD FOR DETERMINING A TREATMENT PARAMETER ON A HAEMOFILTRATION DEVICE, AND HAEMOFILTRATION DEVICE FOR APPLYING THE METHOD

BACKGROUND OF THE INVENTION

1. Field of the Invention

The invention relates to the field of methods for determining treatment parameters on a haemofiltration device as well as haemofiltration devices for such methods.

2. Description of the Related Art

Different methods are used in replacement-of-renal-function treatment. In some of these methods, during treatment, blood is continuously taken from a patient and fed into an extracorporeal circulation system where it flows through a blood cleansing element before it is returned to the patient. Most of the time the blood cleansing element comprises a filter element divided into two chambers by means of a semipermeable membrane, with blood flowing through one chamber of said filter element. Presently, above all, filter elements which comprise thousands of hollow fibres are used for this purpose, with blood flowing through the interior of said hollow fibres.

In the case of haemodialysis, a cleansing fluid (dialysis fluid) flows through the other chamber, with said cleansing fluid absorbing by diffusion the substances to be removed from the blood, such as for example urea, and with said cleansing fluid in relation to substances to be left in the blood, such as electrolytes, having a composition similar to that of healthy blood. By means of a component which controls ultrafiltration, volumes of fluid to be eliminated are also removed from the blood chamber to the dialysis fluid chamber of the filter element.

In the case of haemofiltration, in the other chamber of the filter element, hereinafter referred to as the first chamber, there is not a complete flow of a second fluid instead, only ultrafiltrate is fed to this chamber via the membrane, with said ultrafiltrate then being removed via an ultrafiltrate drainage pipe. During this process, the quantity of fluid is far greater than the quantity which would have to be removed for the patient to attain his/her dry weight. In this way a substantial quantity of substances to be removed such as urea, is removed by convection with the ultrafiltrate. At the same time, almost the entire quantity of fluid is replaced by a substitution fluid which is returned to the patient at a suitable position via the extracorporeal circulation system.

Since convection and diffusion can remove molecules of different sizes with different effectiveness through the membrane, a combination of both processes, called haemodiafiltration treatment, is also used. Modern dialysis machines can alternate between these treatment modes without the need for a complex conversion. Some known devices offer the option of providing the dialysis fluid and the substitution fluid on-line during treatment, using water and a respective concentrate. With these devices it is no longer necessary to have enormous quantities of these fluids (up to approx. 200 litres) at the ready in the form of bags. Such a device is e.g. the subject of EP 0 930 080 A1.

So as to be able to monitor the success of replacement-of-renal-function treatment, the determination of treatment parameters with such blood cleansing apparatus, in particular the effectiveness of the blood cleansing element, is of great interest. Effectiveness is usually expressed by stating the clearance of the blood cleansing element.

Clearance K is defined as the blood stream which is completely freed of a substance (e.g. urea) by the blood cleansing element. In the case of haemodialysis treatment it is a prerequisite that when the dialysis fluid enters the dialyser, said dialysis fluid does not contain any of the substance to be removed. Clearance depends on the area and material of the dialyser and the respective operating conditions (the flow of blood, dialysis fluid and ultrafiltration fluid). Clearance can occur both as a result of diffusion and as a result of convection via the membrane of the filter element, the dialyser.

The term clearance can also be widened so as to cover p substances such as e.g. sodium ions which are already present in the dialysis fluid. This is then called dialysance D which is defined as the blood flow which is completely brought to the concentration level in the dialysis fluid.

From clearance K, the non-dimensional quantity Kt/V can be calculated, where t is the treatment duration and V is the distribution volume of the substance in the human body. It is very common to use Kt/V for urea as the measure of the efficiency of dialysis treatment.

However, measuring the urea concentration has been relatively expensive up to now. Either it necessitates the taking of blood specimens, which is disagreeable to patients and moreover does not allow fast automatic evaluation, or it involves measuring the used dialysis fluid which is still rather expensive.

Presently determining the ionic dialysance provides an alternative. The basic principle of such measurements is based on the fact that the diffusion behaviour of urea and small ions such as $Na^+$, Cl, etc. is almost identical. The concentration of these ions in the dialysis fluid can easily be determined by measuring the electrical conductivity which in turn can be determined using measuring cells which are of relatively simple design. Instead of determining the urea clearance, the ion dialysance is thus determined first. Due to the same diffusion behaviour to be expected, the ion dialysance can then be assumed to be identical to the urea clearance.

In the state of the art there are various publications for calculating the dialysance (e.g. J. Sargent and F. Gotch, in: Replacement of Renal Functions by Dialysis, ed. C. Jacobs et al., Kluwer, Dordrecht, Boston, London, 1996, p. 39). Without ultrafiltration, it can be expressed in the so-called dialysate-side form, in the following equation:

$$D = Qd \frac{Cdo - Cdi}{\alpha Cbi - Cdi}, \qquad (1)$$

where
Qd: Dialysis flow;
Cdo: Concentration of the investigated substance in the outgoing dialysis fluid;
Cdi: Concentration of the investigated substance in the incoming dialysis fluid;
Cbi: Concentration of the investigated substance in the blood streaming into the extracorporeal circulation system (wherein only the volume fraction is to be considered in which this substance is effectively dissolved); and
α: Gibbs-Donnan factor.

The Gibbs-Donnan factor takes into account that on the blood side, charged ions such as for example $Na^+$ are partly bound to oppositely charged proteins which are proteins not commonly found in dialysers. This effect would bring about a situation where in the diffusive equilibrium (at insignificant flows) a somewhat greater ion concentration would occur in the blood plasma when compared to that of the dialysis fluid, because an electrical field counteracts diffusion. For the case of sodium ions in the blood plasma, a case particularly relevant in practical application, $\alpha$ is approx. 0.95. If such accuracy is not required, this factor can be ignored.

In equation 1, all quantities except for Cbi can be measured easily. To do so it is sufficient to arrange two conductivity measuring cells in the dialysis fluid circulation system, with said cells determining the conductivity at the inlet and outlet of the dialyser. The respective conductivity can easily be converted to the concentration Cdi and Cdo. If the concentration Cdi has also been specified and is thus known, for example because precisely defined fluids are used, then there is no need to measure Cdi. Most of the time the dialysis fluid flow Qd is predetermined by the haemodialysis machine and is thus also known. Otherwise it is of course possible to provide respective sensors in addition.

For practical reasons, measuring the conductivity on the blood side is however problematical. It is however possible, by changing the concentration Cdi, to eliminate the term Cbi. This can for example take place in the form of a concentration step or a bole. The former is described in DE 39 38 662 A1; the latter in DE 197 47 360 A1 or WO 00/02604 A1 (we herewith explicitly refer to these publications). Below, both options are considered as alternatives for a change in the concentration of a fresh fluid which is required for blood treatment. The dialysance can then be determined as follows:

$$D = Qd\left(1 - \frac{Cdo2 - Cdo1}{Cdi2 - Cdi1}\right) = Qd\left(1 - \frac{\Delta Cdo}{\Delta Cdi}\right), \quad (2)$$

where
Cdi 1,2: Cdi before and after the change (step), or outside and during the change (bole); and
Cdo 1,2: Cdo before and after the change (step), or outside and during the change (bole).

In the case of a stepped change, $\Delta Cbi$ or $\Delta Cdo$ represent simple differences; in the case of the bole method, they refer to the change integrated via the bole, relative to a base level.

By means of D, it is now possible to determine Cbi by using equation 1. An equivalent approach would be to first determine Cbi as a parameter to be determined from an equation corresponding to equation 2, which results from equation 1 if D is eliminated Further methods are known from the state of the art, such as from WO 98/32476 A1 or EP 0 658 352 A1, which methods do not explicitly make use of equation 2 in determining D, but which in the final analysis are always based on the principle of bringing about a change in the physical-chemical characteristic Cdi, and of holding on to the respective change Cdo in order to permit a statement about the physical-chemical characteristic Cbi on the blood side, or about the filter efficiency D.

Without exception, the state of the art mentions methods which make possible a determination during haemodialysis treatment. There are—at times differing—details as to how the ultrafiltration flow Qf, removed from the blood during haemodialysis treatment, can be taken account of in equations (1) and (2). This is for example the case in EP 1 062 960 A2, wherein Qd is substituted by the sum of the flows Qd and Qf. However, in the case of haemodialysis treatment, the ultrafiltration flow Qf is very small when compared to the dialysis fluid flow Qd and the blood flow Qb, in other words, the interference effect is relatively minor. Typical values for Qf=15 ml/min; for Qd=500 ml/min; and for Qb=300 ml/min.

However, in the case of replacement-of-renal-function treatment, knowledge of the efficiency of the blood cleansing element is of just as much interest in the case of haemofiltration treatment, either on its own or in combination with haemodialysis treatment in the form or haemodiafiltration treatment.

In this connection it is at first not obvious as to how the concept of ion dialysance can be transferred to this case. In haemofiltration there is no dialyser through which a dialysis fluid flows. Moreover, both in haemofiltration and in haemodiafiltration, large quantities of fluid are removed via a haemofilter or haemodialyser and at the same time are added in another location to the extracorporeal blood circulation system. Flows of up to 100 ml/min are achieved which can no longer be considered as being very small when compared to the flow of dialysis fluid (in haemodiafiltration) and when compared to the blood flow.

SUMMARY OF THE INVENTION

It is thus the object of the invention to provide a method with which a treatment parameter can also be determined in a simple manner in haemofiltration treatment, with, just as in previous methods, no measurements to be carried out on the blood side. Furthermore it is the object of the invention to provide a corresponding haemofiltration device for applying the method according to the invention. The case of simultaneous additional haemodialysis treatment (haemodiafiltration) is to be explicitly included, i.e. haemofiltration treatment can also be haemodiafiltration treatment.

This object is met by the method and device according to the present invention, directed to a haemofiltration device comprising a blood cleansing element divided into two chambers by a semipermeable membrane, with a first chamber forming part of an ultrafiltrate outlet system and a second chamber forming part of an extracorporeal blood circulation system. The extracorporeal blood circulation system includes a blood inlet pipe which leads to the second chamber, and a blood outlet pipe which removes blood from the second chamber. The ultrafiltrate outlet system includes an ultrafiltrate outlet pipe, which removes the fluid from the first chamber, and an ultrafiltrate conveyance device for targeted fluid removal from a removal flow Qo through the membrane via the ultrafiltrate outlet pipe. A substitution fluid addition system is provided, having a substitution fluid pipe which leads from a source for the provision of substitution fluid to the extracorporeal blood circulation system, and a substitution conveyance device for conveying substitution fluid in the substitution fluid pipe. A first sensor element is arranged on the substitution fluid pipe for determining a physical-chemical characteristic Cs of the substitution fluid, and a second sensor element is arranged on the ultrafiltrate outlet pipe for determining the corresponding physical-chemical characteristic Cf of the fluid led away. The present invention further includes a device for changing the physical-chemical property Cs of the substitution fluid, and an evaluation and control unit which records first measured values Cs1 and Cf1 of the first and second sensor elements, respectively, and then controls the device for changing the physical-chemical characteristic of the substitution fluid so as to effect a change in said physical-chemical characteristic. Subsequently, the evaluation and control unit records second measured values Cs2 and Cf2 of the first and second sensor elements, respectively, the second values being different from the first values due to the change in the physical-chemical characteristic. From the values Cs1, Cs2, Cf1, Cf2, and Qo, the evaluation and control unit then determines a treatment parameter.

BRIEF DESCRIPTION OF THE DRAWINGS

Below, the invention as well as an exemplary embodiment of a haemodiafiltration device according to the invention are explained in more detail with reference to the drawings. Shown are.

DETAILED DESCRIPTION OF THE PREFERRED EMBODIMENTS

Figure 1:
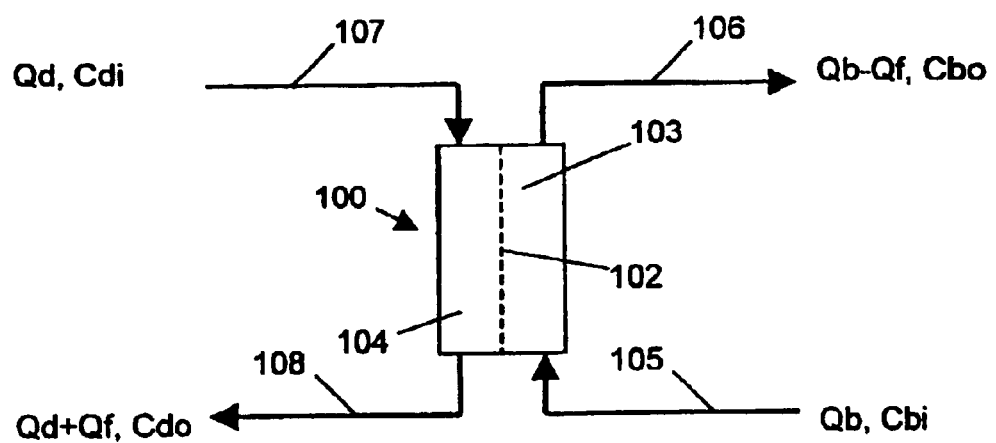
FIG. 1: a diagrammatic representation of the fluid parameters during haemodialysis.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention is based on the surprising recognition that large parts of the formalism applied for haemodialysis can be transposed to haemofiltration provided the parameters involved are correctly allocated. In this respect we refer to FIG. 1: in haemodialysis treatment a haemodialyser 100 which by means of a semipermeable membrane 102 is divided into two chambers 103 and 104, wherein fresh dialysis fluid flows into the first chamber 103 by way of a dialysis fluid inlet pipe 107 with a flow Qd and a physical-chemical characteristic Cdi. A flow Qd+Qf which has been increased by the ultrafiltration flow Qf which is to be removed, flows out from this chamber 103, by way of a dialysis fluid outlet pipe 108, said flow Qd+Qf having the physical-chemical characteristics Cdo. By way of a blood inlet pipe 105, blood at a flow Qb and with the physical-chemical characteristic Cbi, flows into the second chamber 104. A blood flow which has been reduced by the ultrafiltration flow Qf and which has the physical-chemical characteristic Cbo, leaves this chamber 104 via the blood outlet pipe 106.

Figure 2A:
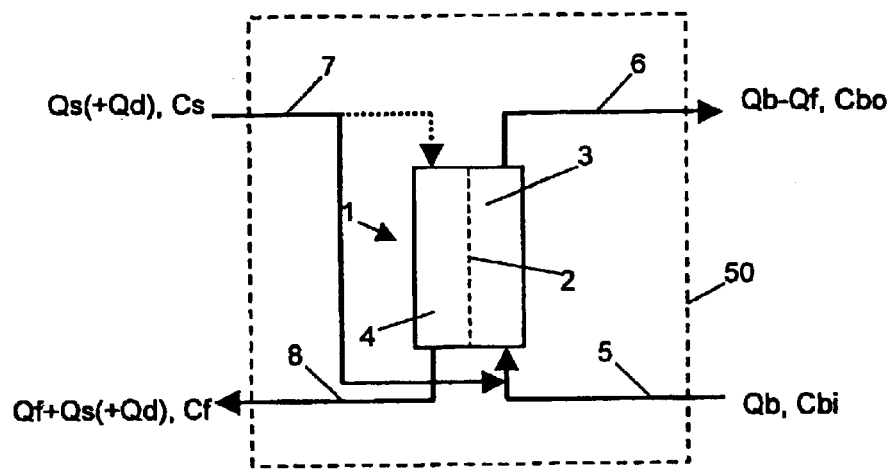
FIG. 2a: a diagrammatic representation of the fluid parameters of haemofiltration with pre-dilution.
Figure 2B:
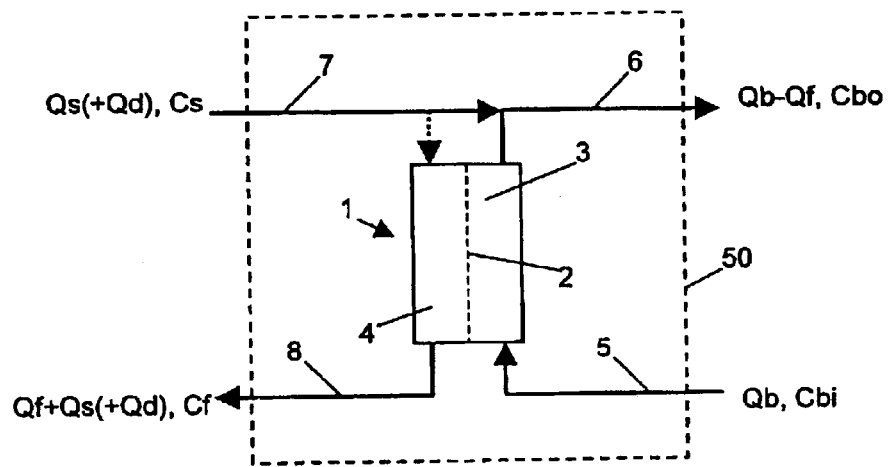
FIG. 2b: a diagrammatic representation of the fluid parameters of haemofiltration with post-dilution.

FIGS. 2a and 2b show a corresponding diagrammatic haemofiltration device in which a haemofilter 1 divided into two chambers 3 and 4 by a semipermeable membrane 2 has been provided as a blood cleansing unit. As far as the blood side is concerned, the same terms apply as have been explained in FIG. 1. Furthermore, a substitution fluid inlet pipe 7 has been provided which is directly connected either to the blood inlet pipe 5 (pre-dilution, FIG. 2a) or the blood outlet pipe 6 (post-dilution, FIG. 2b). Substitution fluid at a flow of Qs and with the physical-chemical characteristic Cs is added directly through said pipe to the extracorporeal blood circulation system, that is to say not via the membrane 2. Furthermore, by way of membrane 2, fluid is removed from the blood at a flow of Qo=Qf+Qs, said fluid flowing into the first chamber 3 and leaving said chamber via the ultrafiltrate outlet pipe 8 with the physical-chemical characteristic Cf.

Furthermore, FIGS. 2a and 2b show a dotted path which branches off the substitution inlet pipe 7 and leads to the first chamber 3. In the case of a haemodiafiltration application, fluid flows through this path in addition. The flow conditions then change to the extent that the terms indicated in brackets, for the dialysis fluid flow Qd, are added. The flow flowing through the ultrafiltrate outlet system is then Qo=Qf+Qs+Qd. The same designations continue to be used for the physical-chemical characteristics Cs and Cf. For the path shown in FIGS. 2a and 2b, Cs remains unchanged by haemodiafiltration. However, the value for Cf will change because now parts of the flow Qd with the physical-chemical characteristic Cs flow through the first chamber and mix with the flow Qs+Qf which is added after flowing through the membrane, so as to be led away together, via the ultrafiltrate outlet pipe B.

Furthermore, in the two FIGS. 2a and 2b there is a box-shaped area 50 each, shown by a dashed line. If this area is regarded as a type of black-box dialyser 1, then the formalisms applying to the arrangements shown in FIG. 1, can surprisingly be transposed to the situation of haemofiltration. If the physical-chemical characteristic is a concentration, in particular the equation corresponding to equation 1 is as follows:

$$D = (Qf + Qs + Qd)\frac{Cf - Cs}{\alpha Cbi - Cs}, \qquad (3)$$

Equation 2 changes to equation 4:

$$D = (Qf + Qs + Qd)\left(1 - \frac{Cf2 - Cf1}{Cs2 - Cs1}\right) = (Qf + Qs + Qd)\left(1 - \frac{\Delta Cf}{\Delta Cs}\right), \qquad (4)$$

The term dialysance can clearly be transposed to this case; dialysance indicates the blood flow which is completely brought to the concentration level of the substitution fluid. This concentration Cs, previously Cdi, represents the maximum concentration to be achieved by blood cleansing. Furthermore, the same analogy observations apply as they were previously made in relation to urea clearance and ion dialysance. It was possible for the applicant to confirm this within the measuring accuracy, in in-vitro experiments in which dialysis fluid enriched with urea was used on the blood side and the urea clearance was directly measured independently.

In this way, devices which were built for operation in haemodialysis devices and are for example based on the methods set out in DE 39 38 662 A1 or DE 197 47 360 A1, can without any problems also be used in haemofiltration devices, taking care of course that the correct concentrations and fluid flows are used.

This is to point out separately one application mode of the method according to the invention. During operation without dialysis fluid in a post-dilution arrangement (FIG. 2b), the method according to the invention seems to have little effect. The change ΔCs is not associated with a direct change ΔCbi which in turn might bring about a change ΔCf. This would equate to ΔCf=0 whereby D=Qf+Qs=Qo, which is to be expected for this case, without it requiring the method according to the invention.

But even for this case, when studied closely, the method according to the invention achieves results which surpass the results expected (to be sure, correspondingly accurate sensor elements are required for this). Just as is the case in haemodialysis, where it was possible to show that a measuring apparatus similar to the arrangement presented here, measures the so-called effective dialysance or clearance (H. D Polaschegg, Int. J. Art Organs 16, 185 (1993)), the same effects also apply in the case of haemofiltration.

Accordingly, the blood Concentration Cbi can nevertheless be changed in the patient by recirculation effects. Even if the effects are minor, the method according to the invention is also suitable for determining the effective dialysance for the case of haemofiltration which is smaller than the expected dialysance D=Qo.

In pre-dilution, a similar expression can be stated for the dialysance to be expected, said expression taking into account that the blood was thinned at a ratio Qs/(Qb+Qs) before it entered the second chamber 4. Here again, as far as effective dialysance is concerned, the same applies as has been said in the context of post-dilution.

The invention is likely to be most significant for haemodiafiltration where the method according to the invention for the first time provides access to dialysance, with the value of dialysance to be expected, in this case not simply being able to be determined from information about flow.

When pre-dilution and pros-dilution are combined, the method according to the invention furthermore offers the advantage in that the respective fraction of substitution fluid for introduction, before and after the second chamber 4, into the extracorporeal blood circulation system, does not have to be known at all. The method automatically determines the correct value of dialysance D.

Figure 3:
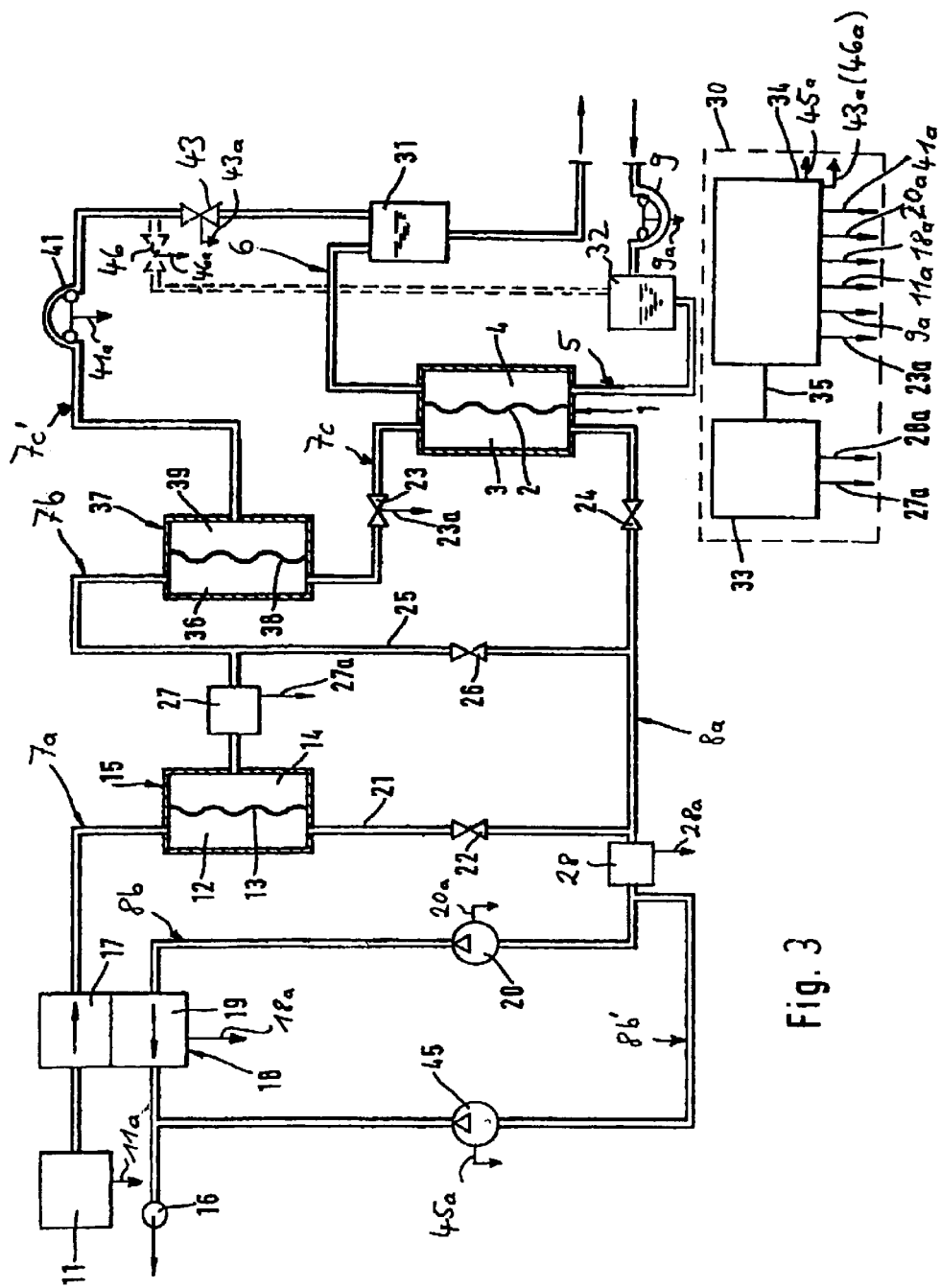
FIG. 3 a diagrammatic representation of an embodiment of a haemofiltration device according to the invention.
Figure 1:
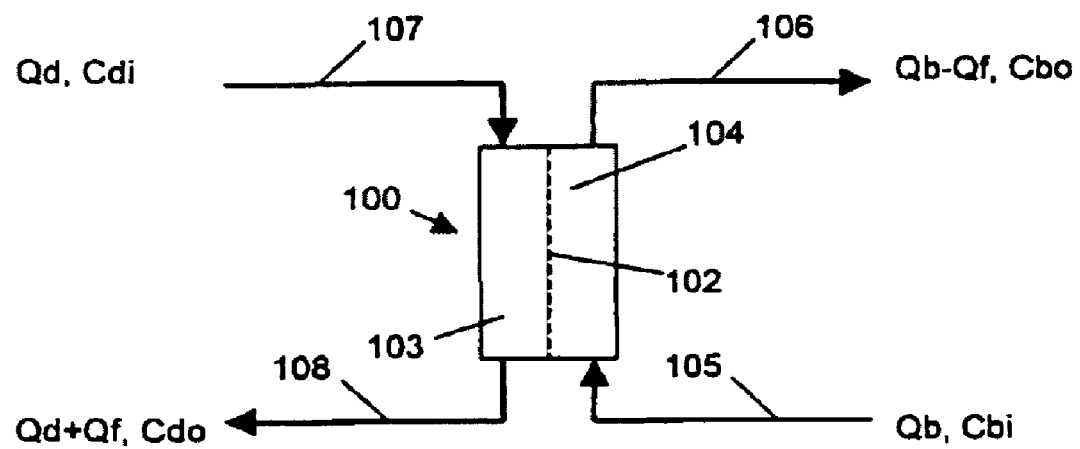
Figure 2A:
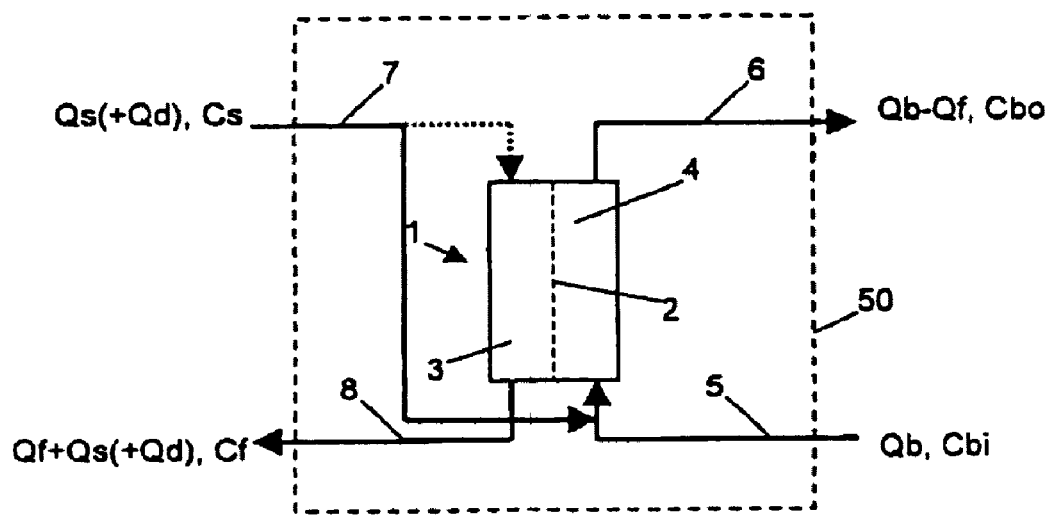
Figure 2B:
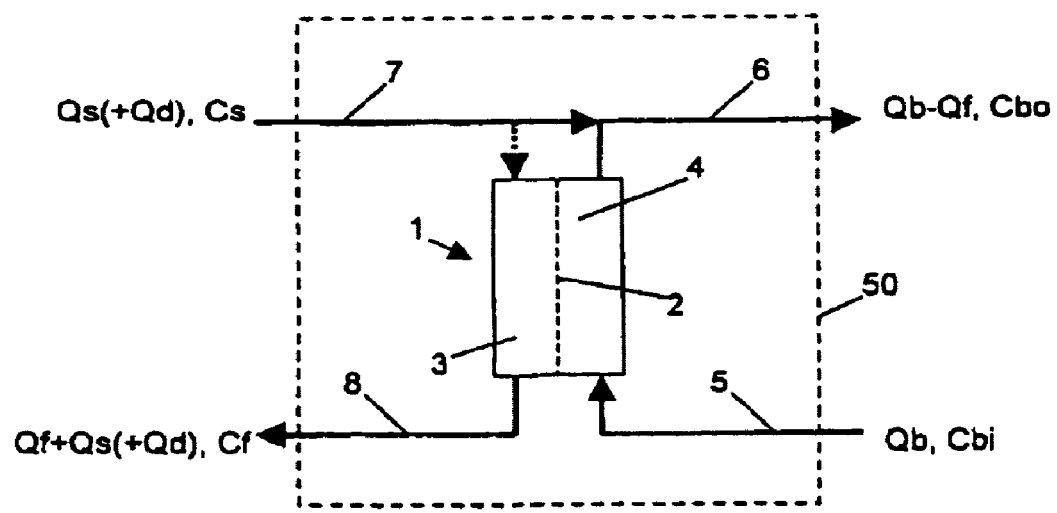

FIG. 3 shows an embodiment of a haemodiafiltration device according to the invention. For applying the method according to the invention. The haemofilter 1 which at the same time can be used as a haemodialyser, forms the core of the haemodiafiltration device. By means of a semipermeable membrane 2, the haemofilter 1 is divided into two chambers 3 and 4, of which the first chamber 3 forms part of an ultrafiltrate outlet system and the second chamber 4 forms part of an extracorporeal blood circulation system.

Apart from the other usual components (not shown in detail), the extracorporeal blood circulation system comprises a blood inlet pipe 5 with a blood feed pump 9 and an arterial bubble trap 32 for supplying blood from a patient to chamber 4, as well as a blood outlet pipe 6 with a venous bubble trap 31 for returning the blood to the patient.

The ultrafiltrate outlet system comprises an ultrafiltrate outlet pipe divided into sections 8a, 8b and 8b'. Section 8a leads from the first chamber 3, with a valve 24 provided for blocking this outlet pipe of the haemofilter. At the end of section 8a a second sensor element is provided as a conductivity measuring cell 28 for detecting the electrical conductivity. With this conductivity measuring cell 28, the ion concentration or predominantly the sodium concentration Cf can be determined in the known manner. To this effect, the measuring cell 28 is connected to a central evaluation and control unit 30, via a data line 28a.

Behind the measuring cell 28, the ultrafiltrate outlet pipe branches into two sections, 8b and 8b'. In each section there is one feed pump. In section 8b this is the dialysis fluid pump/filtrate pump 20 which does not need to be particularly accurate. It only needs to provide adequate feed capacity to fill within a specified time the first half 19 of the balancing chamber of a balancing chamber 18 located in section 8b. Balancing chamber 18 serves to ensure that only a part of the outgoing ultrafiltrate flow moves through section 8b which flow corresponds to the incoming fluid flow in a substitute-fluid supply system (sum of substitution fluid flow Qs and dialysis fluid flow Qd). Advantageously, the balancing chamber 18 comprises two balancing chambers in parallel, so as to ensure a constant flow. For the sake of simplicity the second balancing chamber and the various inlet valves and outlet valves are not shown in FIG. 3.

A volumetric feed pump 45, preferably a membrane pump, is provided in section 8b'. With this pump, the ultrafiltrate flow Qf, which is to be removed in total from the patient, is conveyed. The balancing chamber 18 as well as the pumps 20 and 45 are connected to respective control lines 18a, 20a and 45a, and to the evaluation and control unit 30.

Sections 8b and 8b' finally lead to an outlet 16, but it is immaterial whether the two sections actually unite in the device (as shown) or not.

Fresh substitution fluid and/or dialysis fluid is provided by a fluid source 11 which forms part of a substitution-fluid addition system. The average person skilled in the art has various options when designing the fluid source. Apart from providing the finished solution in bags, this in particular includes preparation of the fluid in the haemodiafiltration device itself, from water and concentrate. For this purpose, the device contains various measuring and control elements which are well known and which are therefore not explained in this document.

The substitution fluid addition system further comprises the following components: the ready-made substitution fluid and/or dialysis fluid flows from the fluid source 11 through a first section 7a of a substitution fluid/dialysis fluid pipe which is followed by sections 7b, 7c and 7c'. The second half 17 of the balancing chamber 18 leads to section 7a. Section 7a then leads to the first chamber 12 of a first sterile filter 15 which is divided into two chambers 12 and 14 by a semipermeable membrane 13. After passing through the membrane 13, the fluid leaves the second chamber 14 of the first sterile filter by way of section 7b of the substitution fluid/dialysis fluid pipe which leads to the first chamber 36 of a second sterile filter 37 which is divided into two chambers 36 and 39 by a semipermeable membrane 38. In section 7b a sensor element 27 is provided, which corresponds to the second sensor element 28, for registering the electrical conductivity of the fluid flowing through this sensor, which in turn is connected to the evaluation and control unit 30 via a data line 27a.

After passing through the membrane 38, the substitution fluid leaves the second chamber 39 of the sterile filter 37 via section 7c' of the substitution fluid pipe. In this section, a feed pump 41 is provided for conveying the substitution fluid flow Qs. A stop valve 43 is provided in front of the position where section 7c' leads into the venous bubble trap 31 (post-dilution). As an alternative or in addition, (shown by a dashed line) section 7c' can lead into the arterial bubble trap (pre-dilution). In this section, a further stop valve 46 is then provided.

From the first chamber 36 of the second sterile filter 37, a section 7c of the dialysis fluid pipe leads to the first chamber 3 of the haemofilter. Section 7c can be closed off by a stop valve 23 which is connected to the evaluation and control unit 30 by way of the control line 23a. With this valve it is thus possible to control whether haemofiltration treatment is to be carried out as pure haemofiltration treatment (valve closed) or as part of haemodiafiltration treatment (valve open). It is also possible to change the treatment mode during treatment.

By means of valves 43 and 46 (control via lines 43a and 46a) if necessary, a change between pre-dilution and post-dilution is possible, or both can even be possible at the same time. To this effect it can be provided for the valves 43 and 46 to be used for flow control or to be supplemented/exchanged by conveyance means of their own, so as to register the ratio of the substitution fluid flow Qs. However, this is of subordinate importance for determining the treatment parameter according to the method according to the invention.

Furthermore, for safety and cleaning functions (not described in further detail), a first bypass pipe 21 is provided which connects the first chamber 12 of the first sterile filter 15 to the section 8a of the ultrafiltrate outlet system, and which bypass pipe 21 can be closed by a valve 22 during normal operation. The same applies to a second bypass pipe 25 which branches from section 7b of the substitution pipe/dialysis fluid pipe and upstream also leads into section 8a of the ultrafiltrate outlet pipe. The second bypass pipe can be closed off by a valve 26.

The haemodiafiltration device further comprises an evaluation and control unit 30 which in turn comprises an evaluation unit 33 and a control unit 34 which are interconnected via a data line 35. The control unit is connected, via the control lines 9a, 11a, 18a, 20a, 23a, 41a, 43a, 45a and 46a, to the various control elements of the haemodiafiltration device, so as to be able to control its operation. Only those control elements/control lines are mentioned which are necessary to understand the invention.

The evaluation unit is connected via data lines with some sensor elements. In the present case these are in particular the two conductivity sensors 27 and 28.

The embodiment of the device according to the invention, in which a first balancing device (17) is provided in the substitution fluid pipe/dialysis fluid pipe (7a, 7b, 7c', 7c) and/or a second balancing device (19, 45) is provided in the ultrafiltrate outlet pipe, has the advantage that with these devices, at the same time the removed flow Qo=Qs+Qf+Qd (relevant for applying equation 4) can be determined. In the embodiment according to FIG. 3, the volume of a balancing chamber fill is known very precisely. By way of the frequency of the balancing chamber cycles, the flow Qs+Qd can be determined very precisely. Pump 45 is a volumetric pump and can thus also be used to determine the flow Qf—in the present example the pump is a membrane pump and the flow is determined via the frequency of pump strokes and the known stroke volume. This eliminates inaccuracies which for example occur in the case of a substitution fluid pump 41 designed as a roller pump, whose feed quantity can fluctuate within a certain range due to tolerance fluctuations in the pump hose segment and also due to fluctuations in charge pressure.

In the application of the method according to the invention, the evaluation and control unit 30 takes the following process steps: the fluid source 11 is controlled in such a way that it provides substitution fluid at a concentration of Cs1. This concentration is registered via the first measuring sensor 27 and transmitted to the evaluation unit 33. The fluid flows Qb, Qs, Qf and Qd are set at the conveying devices/pumps 9, 18, 20, 41 and 45 and the valves 23, 43 and 46 are opened or closed, depending on the operating mode. Furthermore, the values of Qb, Qs, Qf and Qd are transmitted from the control unit 34 to the evaluation unit 33. The concentration values Qf1 are recorded by the second measuring sensor 28 and transmitted to the evaluation unit 33.

At a point in time when the control sequence provides for this automatically, or when this was caused for some other reason, e.g. manually, following instructions by the control unit 34, the fluid source 11 carries out a change in the sodium concentration of the substitution fluid, e.g. in bole shape, i.e. the sodium concentration is temporarily changed before resuming the initial value. (Where substitution fluid is provided in the form of bags, this can take place by an automatic or manual injection station (not shown) acting on the substitution fluid pipe section 7a). The respective concentrations Cs2 and Cf2 are recorded and transmitted to the evaluation unit 33. After decay of the bole, the evaluation unit 33 determines as a treatment parameter the ion dialysance or the urea clearance of the haemodiafiltration device, by first determining the integrated differences ΔCs and ΔCf between the original concentrations Cs1 and Cf1 and the concentrations Cs2 and Cf2 which were changed during the bole, before determining the ion dialysance and thus the urea clearance by means of equation 4. This value can then be displayed on a display unit (not shown) which usually forms part of such blood treatment devices anyway.

Measuring can be repeated automatically at specified intervals (e.g. 30 min.); in this way it is possible to determine urea clearance throughout the entire haemofiltration treatment. By integration over time, the evaluation unit 33 can determine the parameter Kt which either on its own or by means of a previously entered or otherwise determined value for the distribution volume V, is converted to form the treatment efficiency parameter kt/V and is displayed. The values determined can of course also be used to adjust the further progress of treatment by way of the control unit 34 so that a desired treatment objective can actually be achieved.

According to a particularly preferred improvement of the invention, the haemodiafiltration device is also able, after initial determination of the ion dialysance D, to calculate further values of dialysance for future points in time when at least one of the flows Qs, Qf, Qd or Qb has changed. In routine measuring, ions are transferred to the blood. Consequently, such measuring should not be carried out too frequently, even if it can be mutually compensated for by positive and negative boles and if individually they do not have any effect on the patient. This is also sensible because otherwise, during measuring which can take a few minutes, the variation options of other treatment parameters can be limited. For a similar reason, a method for haemodialysis has become known which can determine dialysance changes caused only by flow changes, without the need for renewed measuring. This method is described in publication EP 1 062 960 A2 by he applicant, to which publication reference is expressly made.

It is thus desirable to have such simplification available also when determining the dialysance in haemofiltration. A development of the invention thus provides for the evaluation and control unit 30 to be in a position, between two instances of measuring the dialysance, to automatically determine a new dialysance value if a change in flow conditions has been registered, without having to engage in measuring. To this effect, the evaluation unit 33 continuously evaluates the values for Qf, Qs, Qd and Qb, transmitted via the line 35. As soon as there is a change in relation to a previously determined first set Qf1, Qs1, Qd1 and Qb1, for which a dialysance D1 was determined and saved, the evaluation unit 33 determines a new dialysance D2 for the new, second, set Qf2, Qs2, Qd2 and Qb2 The evaluation unit 33 proceeds as follows:

By means of equation 5, the evaluation unit 33 first determines the diffusive fraction of dialysance D1:

$$D1 diff = \frac{Qb1 + kQs1}{Qb1 - Qf1 - (1-k)Qs1}\left(\frac{Qb1 + kQs1}{Qb1}D1 - Qf1 - Qs1\right) \quad (5)$$

where K=1 in the case of pre-dilution and K=0 in the case of post-dilution. Next the filter coefficient k0A is determined which is assumed to be constant between the two points in time, 1 and 2:

$$kOA = \frac{(Qb1 + kQs1)Qd1}{Qd1 - Qb1 - kQs1} \ln \frac{\frac{D1diff}{Qd1} - 1}{\frac{D1diff}{Qb1 + kQs1} - 1}, \quad (6)$$

With this expression for k0A it is now possible to determine the diffusive dialysance D2diff for the second set of flows according to equation 7:

$$D2diff = Qb2 \frac{e^{\gamma} - 1}{e^{\gamma} - \frac{Qb2}{Qd2}}, \; mity = koA \frac{Qd2 - Qb2}{Qb2 Qd2}, \quad (7)$$

D2diff can now be inserted into equation 5 which after exchanging the first set Qb1, Qs1, Qf1 for the second set Qb2, Qs2, Qf2, can be resolved to D2.

The invention thus provides a simple and uncomplicated method for determining a treatment parameter during haemofiltration and haemodiafiltration, wherein it is possible to fall back on a method that is well proven in haemodialysis. A respective haemo(dia)filtration device only needs to be slightly modified so that the method can be automated.

The invention being thus described, it will be apparent that the same maybe varied in many ways. Such variations are not to be regarded as a departure from the spirit and scope of the invention, and all such modifications as would be recognized by one skilled in the art are intended to be included within the scope of the following claims.

What is claimed is:

1. A method for determining a treatment parameter on a haemofiltration device having a blood cleansing element divided into first and second chambers by a semipermeable membrane, said first chamber forming part of an ultrafiltrate outlet system and said second chamber forming part of an extracorporeal blood circulation system, the device also having a substitution-fluid addition system with which substitution fluid can be added to the extracorporeal blood circulation system, the method comprising the steps of:

determining a fluid flow Qo led away from the first chamber;

determining a first physical-chemical characteristic Cs1 in the substitution fluid and a corresponding first physical-chemical characteristic Cf1 in the fluid led away;

changing the physical-chemical characteristic Cs in the substitution fluid;

determining a second physical-chemical characteristic Cs2 in the substitution fluid and a second corresponding physical-chemical characteristic Cf2 in the fluid led away; and determining a treatment parameter from the determined values of the fluid flow Qo led away, the physical-chemical characteristics Cs1 and Cs2 in the substitution fluid, and the physical-chemical characteristics Cf1 and Cf2 in the fluid led away.

2. The method according to claim 1, wherein the change in the physical-chemical characteristic Cs is step-shaped or bole-shaped.

3. The method according to claim 2, wherein the treatment parameter is a dialysance of the blood cleansing element, and is determined according to the following expression, with $\Delta Cf = Cf2 - Cf1$ and $\Delta Cs = Cs2 - Cs1$:

$$D = \left(1 - \frac{\Delta Cf}{\Delta Cs}\right) \cdot Qo.$$

4. The method according to claim 1, wherein the treatment parameter is a blood input concentration Cbi.

5. The method according to claim 1, further comprising the steps of:

determining an ultrafiltrate flow Qf removed in total from the extracorporeal circulation system as a first value;

determining a substitution fluid flow Qs as a second value;

determining, from a sum of the first and second values, the removed fluid flow Qo.

6. The method according to claim 1, further comprising the steps of:

admitting dialysis fluid at a flow Qd into the first chamber; and determining the removed fluid flow Qo as a sum of an ultrafiltrate flow Qf removed in total from the extracorporeal circulation system, a substitution fluid flow Qs and the added flow Qd.

7. The method according to claim 6, wherein a blood flow Qb is determined as the effective blood plasma flow which flows into the blood inlet pipe and in which the change in the physical-chemical characteristic can have an effect.

8. The method according to claim 7, wherein a first dialysance value D1 is determined in a first set of flows Qd1, Qb1, Qs1 and Qf1 and subsequently a second dialysance value D2 is calculated for a second set of flows Qd2, Qb2, Qs2 and Qf2, based on the values of the first set of flows and D1.

9. The method according to claim 8, wherein based on several dialysance values D1i determined at various points in time i during haemofiltration treatment, and several dialysance values D2j calculated at various points in time j during haemofiltration treatment, a total treatment efficiency Kt achieved is determined by summation of the corresponding dialysance values, multiplied by a time difference to the previous or subsequent instance of measuring/calculation.

10. A haemofiltration device comprising:

a blood cleansing element divided into two chambers by a semipermeable membrane, with a first chamber forming part of an ultrafiltrate outlet system and a second chamber forming part of an extracorporeal blood circulation system;

said extracorporeal blood circulation system including a blood inlet pipe which leads to the second chamber, and a blood outlet pipe which removes blood from the second chamber;

said ultrafiltrate outlet system including an ultrafiltrate outlet pipe which removes the fluid from the first chamber, and an ultrafiltrate conveyance device for targeted fluid removal from a removal flow Qo through the membrane via the ultrafiltrate outlet pipe;

a substitution fluid addition system having a substitution fluid pipe which leads from a source for the provision of substitution fluid to the extracorporeal blood circulation system, and a substitution conveyance device for conveying substitution fluid in the substitution fluid pipe;

a first sensor element arranged on the substitution fluid pipe for determining a physical-chemical characteristic Cs of the substitution fluid;

a second sensor element arranged on the ultrafiltrate outlet pipe for determining the corresponding physical-chemical characteristic Cf of the fluid led away;

a device for changing the physical-chemical property Cs of the substitution fluid; and an evaluation and control unit which records first measured values Cs1 and Cf1 of the first and second sensor elements, respectively, and then controls said device for changing the physical-chemical characteristic of the substitution fluid so as to effect a change in said physical-chemical characteristic; said evaluation and control unit recording second measured values Cs2 and Cf2 of the first and second sensor elements, respectively, said second values having changed from said first values because of the change in said physical-chemical characteristic; and said evaluation and control unit determining a treatment parameter from the values Cs1, Cs2, Cf1, Cf2, and Qo.

11. The haemofiltration device according to claim 10, wherein the evaluation and control unit controls the device for changing the physical-chemical characteristic of the substitution fluid such that the change is step-shaped or bole-shaped.

12. The haemofiltration device according to claim 11, wherein the treatment parameter is a dialysance of the blood cleansing element, and the evaluation and control unit determines the dialysance according to the following expression, with $\Delta Cf = Cf2 - Cf1$ and $\Delta Cs = Cs2 - Cs1$:

$$D = \left(1 - \frac{\Delta Cf}{\Delta Cs}\right) \cdot Qo.$$

13. The haemofiltration device according to claim 10, wherein the treatment parameter is a blood input concentration Cbi.

14. The haemofiltration device according to claim 10, wherein the evaluation and control unit saves set values and/or measured values for a total ultrafiltrate flow Qf to be removed from the extracorporeal blood circulation system, and a substitute-fluid flow Qs, and as a sum of these two flows Qf, Qs, determines the removal flow Qo.

15. The haemofiltration device according to claim 10, wherein the source for providing substitution fluid is also a source for providing dialysis fluid, from which source a dialysis fluid inlet pipe leads to the first chamber.

16. The haemofiltration device according to claim 15, wherein the evaluation and control unit saves the removal flow Qo as the sum of set values and/or measured values for a total ultrafiltrate flow Qf to be removed from the extracorporeal blood circulation system, a substitute-fluid flow Qs, and a dialysis fluid flow Qd flowing into the first chamber.

17. The haemofiltration device according to claims 15, wherein an inlet portion of the substitution fluid pipe and the dialysis fluid inlet pipe are a common pipe in a first section and, after branching off, are separate pipes in a second section.

18. The haemofiltration device according to claim 10, further comprising a first balancing device in the substitution fluid pipe and a second balancing device in the ultrafiltrate outlet system.

19. The haemofiltration device according to claim 18, wherein the ultrafiltrate outlet pipe branches into a first pipe and a second pipe, the first pipe passing through a first part of the second balancing device, said second pipe including a device for conveying a total ultrafiltrate flow Qf to be removed from the extracorporeal circulation system as a second part of the second balancing device, said substitution fluid pipe passing through the first balancing device, said first balancing device and said first part of said second balancing device forming a balancing chamber.

20. The haemofiltration device according to claim 18, wherein at least one of the first and second balancing devices is designed such that a sum of a substitution fluid flow Qs and a dialysis fluid flow Qd can be determined and can be acquired by the evaluation and control unit.

21. The haemofiltration device according to claim 20, wherein at least one of the first and second balancing devices is designed so that, from the flows flowing therethrough, a total ultrafiltrate flow Qf to be removed from the extracorporeal circulation system can be determined and can be acquired by the evaluation and control unit.

22. The haemofiltration device according to claim 10, wherein an inlet portion of the substitution fluid pipe leads into the blood outlet pipe (post-dilution).

23. The haemofiltration device according to claim 10, wherein an inlet portion of the the substitution fluid pipe leads into the blood inlet pipe (pre-dilution).

24. The haemofiltration device according to claim 10, wherein the physical-chemical characteristic is a concentration.

25. The haemofiltration device according to claim 24, wherein the first and second sensor elements are conductivity sensors.

26. The haemofiltration device according to claim 21, wherein the evaluation and control unit saves a blood flow Qb as an effective fluid flow which flows into the blood inlet pipe and in which the change of the physical-chemical characteristic can have an effect.

27. The haemofiltration device according to claim 26, wherein the evaluation and control unit saves a first dialysance value D1 in a first saved set of flows Qd1, Qb1, Qs1 and Qf1 and on the basis of these values calculates a second dialysance value D2 for a second set of flows Qd2, Qb2, Qs2 and Qf2.

28. The haemofiltration device according to claim 27, wherein the evaluation and control unit, based on several saved dialysance values D1i determined at various points in time i during haemofiltration treatment, and several saved dialysance values D2j calculated at various points in time j during haemofiltration treatment, determines a treatment efficiency Kt achieved, by summation of the corresponding dialysance values, multiplied by a time difference to the previous or subsequent instance of measuring/calculation.

29. The haemofiltration device according to claim 10, further comprising a display device on which the treatment parameter can be displayed.

30. The haemofiltration device according to claim 29, wherein the treatment parameter displayed is selected from the group consisting of a dialysance D, interim results and an actual treatment efficiency Kt.

* * * * *

UNITED STATES PATENT AND TRADEMARK OFFICE
CERTIFICATE OF CORRECTION

PATENT NO. : 6,939,471 B2
APPLICATION NO. : 10/393361
DATED : September 6, 2005
INVENTOR(S) : Gross et al.

It is certified that error appears in the above-identified patent and that said Letters Patent is hereby corrected as shown below:

Drawing sheets 1 and 2, containing Figs. 1, 2a and 2b, are to be replaced with attached drawing sheets 1 and 2.

Col. 1, line 39, change "complete flow of a second fluid instead" to
--complete flow of a second fluid. Instead--;

Col. 2, line 12, delete "p" after "cover";

Col. 6, line 13, change "B" to --8--;

Col. 7, line 1, change "Concentration" to --concentration--;

line 25, change "invention. For" to --invention for--;

Col. 10, line 15, insert --,-- between "which" and "either";

line 18, change "kt" to --Kt--;

Col. 11, line 28, change "maybe" to --may be--;

Col 13, line 50, Claim 17, line 1, change "claims" to --claim--.

Signed and Sealed this

Third Day of October, 2006

JON W. DUDAS
*Director of the United States Patent and Trademark Office*